United States Patent [19]

Gruetsmacher et al.

[11] 4,289,702

[45] Sep. 15, 1981

[54] PREPARATION OF ERYTHORBIC ACID AND ASCORBIS ACID 6-FATTY ACID ESTERS

[75] Inventors: Gordon D. Gruetsmacher, Gales Ferry; Charles R. Stephens, East Lyme, both of Conn.

[73] Assignee: Pfizer Inc., New York, N.Y.

[21] Appl. No.: 156,746

[22] Filed: Jun. 5, 1980

Related U.S. Application Data

[63] Continuation of Ser. No. 75,084, Sep. 13, 1979, abandoned, which is a continuation of Ser. No. 861,506, Dec. 16, 1977, abandoned.

[51] Int. Cl.$^3$ ............................................ C07D 307/62
[52] U.S. Cl. ................................................... 260/343.7
[58] Field of Search ......................... 260/410.6, 343.7

[56] References Cited

U.S. PATENT DOCUMENTS 3,250,790  5/1966  Klaui et al. ...................... 260/343.7
3,551,464  12/1970  Miller et al. ..................... 260/410.6

OTHER PUBLICATIONS

Cousins et al., JOCS vol. 54, pp. 708–312 (1977).
Swun et al., Oil and Soap, Nov. 1943, pp. 224–226.

*Primary Examiner*—John F. Niebling
*Attorney, Agent, or Firm*—Connolly and Hutz

[57] ABSTRACT

A process for the preparation of erythorbic acid and ascorbic acid 6-fatty acid esters using liquid anhydrous hydrogen fluoride as catalyst and solvent.

6 Claims, No Drawings

PREPARATION OF ERYTHORBIC ACID AND ASCORBIS ACID 6-FATTY ACID ESTERS

CROSS-REFERENCE TO RELATED APPLICATIONS

This is a continuation of application Ser. No. 075,084 filed Sept. 13, 1979, now abandoned, which is a continuation of application Ser. No. 861,506 filed Dec. 16, 1977, now abandoned.

BACKGROUND OF THE INVENTION

This invention concerns erythorbic and ascorbic acids. More specifically, it concerns the preparation of fatty acid monoesters of these compounds.

Erythorbic and ascorbic acids, because of their nontoxic nature and strong reducing power, are commonly used as antioxidants in food. In exploiting this antioxidant property with foods of high fat content, erythorbic acid and ascorbic acid 6-fatty acid esters, which possess a higher fat solubility with retained reducing power, are preferred. These esters are additionally used as emulsion stabilizers in food preparations, and the ascorbic acid ester may also serve as a source of Vitamin C.

These fatty acid monoesters of erythorbic and ascorbic acids, such as erythorbic acid 6-palmitate, are currently prepared utilizing concentrated sulfuric acid as catalyst and solvent. In such preparations, one of the reactants is routinely used in excess. The fatty acid, being the less expensive ingredient, is normally selected, although preparations in which the fatty acid is the limiting ingredient have also been reported (Oil and Soap, 20, page 224, 1943). In either case, the yield to monoester is only about 50 percent. A further drawback of this system is the difficulty encountered in separating the product from the excess reactant, particularly in the case of excess fatty acid. It is therefore the object of this invention to overcome such difficulties.

While it is known from U.S. Pat. No. 3,551,464 that anhydrous hydrogen fluoride can be employed in the esterification of simple polyols such as glycerol, it was never recognized that this medium would be useful for the esterification of erythorbic or ascorbic acid.

SUMMARY OF THE INVENTION

Now it has been unexpectedly found that anhydrous hydrogen fluoride is not only useful, but indeed offers substantial advantages, as reaction solvent and catalyst for the high yield preparation of erythorbic and ascorbic acid 6-fatty acid esters in a simple and convenient manner. Accordingly, the present invention entails a process for the monoesterification of erythorbic or ascorbic acid with a saturated fatty acid of from about 12 to 18 carbon atoms in the presence of at least about 10 moles of anhydrous hydrogen fluoride per mole of the fatty acid to form the erythorbic acid or ascorbic acid 6-fatty acid ester. Preferably, the fatty acid is lauric acid or palmitic acid, the erythorbic or ascorbic acid is employed at a level of about one mole per mole of the fatty acid and the hydrogen fluoride is present in the amount of from about 25 to 50 moles per mole of fatty acid.

DETAILED DESCRIPTION OF THE INVENTION

The process of the present invention results in esterification of erythorbic and ascorbic acids specifically at the C-6 primary alcohol. Such monoesterification is accomplished in high yield, as disclosed hereinafter, when using only stoichiometric quantities of reactants, mild reaction conditions and short reaction times.

While both of the optical isomers of either erythorbic acid or ascorbic acid may be used in the practice of this invention, the natural isomer, namely D-erythorbic acid or L-ascorbic acid, is commonly employed.

Fatty acids are those carboxylic acids derived from or contained in animal or vegetable fat or oil. They are generally composed of a chain, either straight or branched, of alkyl groups terminating in a carboxyl radical. The acid may be saturated or unsaturated and either solid, semisolid or liquid in form. Fatty acids suitable for the practice of this invention are those saturated acids containing from about 12 to 18 carbon atoms, including lauric, myristic, palmitic and stearic. With saturated acids having less than about 12 carbon atoms, the monoester product tends to be too water soluble for practical recovery, while with such acids having more than about 18 carbon atoms, the starting acid is inclined to require an inordinate amount of solvent for suitable reaction and the monoester product may be too oil insoluble for suitable use. Unsaturated fatty acids do not appear to lend themselves to this reaction system. Preferred are lauric acid and palmitic acid.

Liquid anhydrous hydrogen fluoride serves as both the reaction solvent and catalyst. In order to ensure the essential solution of the fatty acid in the solvent under the reaction conditions employed, at least about 10 moles of hydrogen fluoride per mole of fatty acid is used. Additional solvent results in improved product yield, and about 25 to 50 moles of hydrogen fluoride per mole of fatty acid is therefore preferred. At the especially preferred solvent level of about 50 moles of hydrogen fluoride per mole of fatty acid, the reaction yield is nearly quantitative, and while a greater amount of the solvent may be used without detriment, little economic advantage exists for such usage.

The reactants are preferably combined in the solvent in about stoichiometric amounts, i.e., about one mole of erythorbic or ascorbic acid per mole of the fatty acid. While reactant amounts other than stoichiometric, such as 20 to 30 percent excess either of the fatty acid or of the erythorbic or ascorbic acid may be used, such use simply complicates the product recovery and increases the raw materials cost.

The esterification, while conveniently carried out over a wide range of temperature of from about 0° to 75° C., is normally run at about 10° to 50° C., preferably at about 20° to 30° C. and most preferably at about 20° to 23° C. Since the hydrogen fluoride solvent has a normal boiling point of about 20° C., reactions at much above this temperature will be at superatmospheric pressure. The reaction time depends upon the reaction temperature, and is normally about 1 to 2 hours at reaction temperatures of 20° to 30° C.

The product monoester is isolated from the final reaction mixture by standard isolation techniques. Thus, for example, the reaction mixture may be cooled and the bulk of the hydrogen fluoride solvent removed by distillation at reduced pressure. The reaction may then be diluted with an essentially water-insoluble solvent such as methyl isobutyl ketone or diethyl ether and washed with an aqueous solution of an inorganic base such as sodium or potassium hydroxide to remove the remaining hydrogen fluoride and any unreacted erythorbic or ascorbic acid. The final pH of the wash solution is preferably about 3 to 4 to prevent salt formation with any unreacted fatty acid, such salt formation tending to cause emulsification and consequent phase separation problems. The washed organic layer may then be concentrated to remove the organic solvent and water, and the concentrate then diluted with an appropriate nonpolar organic solvent such as hexane or petroleum ether to dissolve any excess fatty acid and allow the product monoester to separate.

The disclosed process, with its capability of producing erythorbic acid and ascorbic acid 6-fatty acid esters in high yield using only stoichiometric amounts of the reactants, mild temperatures and short reaction times, thus offers a surprisingly simple, economic and productive method for this preparation. This is in contrast to alternative preparations such as those in concentrated sulfuric acid as disclosed by Cousins et al, Journal of the American Oil Chemists' Society, 54, page 308 (1977), wherein excess reagent and long reaction time are required.

The following examples are merely illustrative of the process of the present invention and are not to be construed as limiting the invention, the scope of which is defined by the appended claims.

EXAMPLE 1

Erythorbic acid[1] (17.6 g, 0.10 mole), palmitic acid[2] (25.6 g, 0.10 mole) and anhydrous hydrogen fluoride[3] (50 ml 2.5 moles) were mixed in a capped 250 ml polyethylene bottle at 0° C. by means of a magnetic stirring bar. The cooling bath was removed, and the mixture was warmed to 22°–3° C. and stirred at that temperature for 1.5 hours. The reaction mixture was then added to 500 ml of methyl isobutyl ketone (MIBK), and the resulting solution was cooled to 0° C. and washed with 400 ml of 6.25 N aqueous potassium hydroxide at less than 25° C. to remove the hydrogen fluoride and any unreacted erythorbic acid. The aqueous layer was separated, and the organic layer was washed with 200 ml of deionized water and concentrated at less than 40° C. to 250 ml. The essentially water-free concentrate was diluted with 750 ml of hexane and stirred for 2 hours in an ice bath. The resulting slurry was vacuum filtered, and the filter cake was washed with hexane and dried overnight in a vacuum oven at 40° C. to give 33.69 g of a white waxy solid assaying 98.3% erythorbic acid 6-palmitate (0.080 mole, 80% yield) as determined by iodine titration. Thin layer chromatography indicated the product to be one component.

When the above esterification was repeated substituting ascorbic acid[4] for erythorbic acid, 35.12 g of a white waxy solid assaying 94.3% ascorbic acid 6-palmitate (0.080 mole, 80% yield) was obtained.

The above esterifications may be repeated substituting L-erythorbic acid and D-ascorbic acid for their natural optical isomers with comparable results.

(1) D-Erythro-hex-2-enonic acid, γ-lacetone; FCC grade; Pfizer Inc., New York, New York
(2) Technical grade; Pfaltz and Bauer Inc., Stamford, Conn.
(3) Matheson Gas Products, East Rutherford, N.J.
(4) L-Ascorbic acid; USP grade; Pfizer Inc.

EXAMPLE 2

The procedure of Example 1 was repeated with the exception that myristic acid[1] (22.8 g 0.10 mole) was substituted for the palmitic acid. The resulting white waxy solid weighed 30.95 g and assayed 99.9% erythorbic acid 6-myristate (0.080 mole, 80% yield).

(1) Technical grade; Matheson, Coleman and Bell, East Rutherford, N.J.

EXAMPLE 3

The procedure of Example 1 was repeated with the exception that stearic acid[1] (28.5 g, 0.10 mole) was substituted for the palmitic acid. The resulting white waxy solid weighed 37.04 g and assayed 95.6% erythorbic acid 6-stearate (0.080 mole, 80% yield).

(1) Technical grade; Pfaltz and Bauer Inc.

EXAMPLE 4

Erythorbic acid (17.6 g, 0.10 mole), lauric acid[1] (20.0 g 0.10 mole) and anhydrous hydrogen fluoride (25 ml, 1.25 moles) were mixed in a capped polyethylene bottle at 0° C. as in Example 1. The cooling bath was removed, and the reaction mixture was warmed to and stirred for 1.5 hours at 22°–3° C. and then processed as in Example 1. The resultant white waxy solid weighed 25.68 g and assayed 97.6% erythorbic acid 6-laurate (0.070 mole, 70% yield).

Repetition of the preparation substituting ascorbic acid for the erythorbic acid resulted in the isolation of 26.35 g of a white waxy solid assaying 95.1% ascorbic acid 6-laurate (0.070 mole, 70% yield).

(1) Technical grade; J. T. Baker Chemical Company, Phillipsburg, N.J.

EXAMPLE 5

Erythorbic acid (17.6 g, 0.10 mole), palmitic acid (25.6 g, 0.10 mole) and anhydrous hydrogen fluoride (37.5 ml, 1.88 moles) were mixed in a polytetrafluoroethylene-lined steel bomb at 0° C. The bomb was capped, heated to and held at 30° C. for 1.5 hours, then cooled to 0° C. and opened. The resultant gel-like reaction mixture was processed following the procedure of Example 1 with the exception that 300 ml rather than 400 ml of 6.25 N aqueous potassium hydroxide was used. The resultant white waxy solid weighed 32.47 g and assayed 96.9% erythorbic acid 6-palmitate (0.076 mole, 76% yield).

EXAMPLE 6

Erythorbic acid (17.6 g, 0.10 mole) palmitic acid (25.6 g, 0.10 mole) and anhydrous hydrogen fluoride (100 ml, 5.0 moles) were mixed in a capped polyethylene bottle at 0° C. as in Example 1. The cooling bath was removed and the reaction mixture was warmed to and stirred for 1.5 hours at 22°–3° C. The reaction vessel was the connected to a vacuum system equipped with two traps cooled by a dry ice-acetone mixture and finally to an aqueous potassium hydroxide scrubber. The system pressure was gradually reduced to 150 mm Hg, resulting in collection of 62.5 ml (3.1 moles) of hydrogen fluoride from the reaction mixture in the traps. The remaining reaction mixture was then processed as in Example 1 to give 41.10 g of a white waxy solid assaying 95.7% erythorbic acid 6-palmitate (0.095 mole, 95% yield).

The esterification can be repeated with comparable results by using 0.12 mole (20 percent molar excess) rather than the 0.10 mole of either the erythorbic acid or the palmitic acid or by substituting lauric acid for the palmitic acid.

EXAMPLE 7

Erythorbic acid (3.54 g, 0.02 mole) and palmitic acid (5.11 g, 0.02 mole) were combined in a 25 ml polytetrafluoroethylene liner for a stainless steel bomb. The liner and its contents were inserted into the bomb and cooled to 0° C. Anhydrous hydrogen fluoride (5 ml, 0.25 mole) was pipetted into the bomb, the liner cover and bomb cap were quickly closed, and the bomb contents was heated to and stirred for 1 hour at 50° C. using a magnetic stirring bar. The bomb was then cooled in an ice bath to 0° C. and opened. The viscous reaction mixture was transferred with about 75 ml of MIBK to a polyethylene flask, and the resultant solution was cooled to 0° C. and washed with 350 ml of 0.56 N aqueous potassium hydroxide at less than 25° C. The neutralized organic layer was washed with 100 ml of deionized water, dried over 15 g of 4 A molecular sieves, diluted with 350 ml of hexane and placed in a refrigerator overnight. The resulting slurry was vacuum filtered, and the filter cake was washed with hexane and dried overnight in a vacuum oven at 40° C. to give 5.53 g of a white waxy solid assaying 93.0% erythorbic acid 6-palmitate (0.0124 mole, 62% yield).

What is claimed is:

1. A process for the preparation of a 6-fatty acid ester of erythorbic or ascorbic acid which comprises contacting erythorbic or ascorbic acid with a saturated fatty acid of from about 12 to 18 carbon atoms in a medium consisting essentially of at least about 10 moles of anhydrous hydrogen fluoride per mole of said fatty acid and continuing said contacting until monoesterification is substantially complete.

2. The process of claim 1 wherein said fatty acid is lauric acid or palmitic acid.

3. The process of clam 1 wherein said erythorbic or ascorbic acid is employed at a level of about one mole per mole of said fatty acid.

4. The process of claim 1 wherein said hydrogen fluoride is in the amount of from about 25 to 50 moles per mole of said fatty acid.

5. The process of claim 1 wherein said reaction is conducted at a temperature of from about 20° to 30° C.

6. A process for the monoesterification of erythorbic acid with lauric acid to erythorbic acid 6-laurate, which comprises contacting about stoichiometric equivalents of said reactants in a medium consisting essentially of about 50 molar equivalents of anhydrous hydrogen fluoride at a temperature of from about 20° to 30° C. until said monoesterification is substantially complete.

* * * * *